United States Patent [19]

Drewlow

[11] Patent Number: Plant 6,116

[45] Date of Patent: Feb. 23, 1988

[54] POINSETTIA PLANT NAMED MIRABELLE

[75] Inventor: Lyndon W. Drewlow, Ashtabula, Ohio

[73] Assignee: Mikkelsens Inc., Ashtabula, Ohio

[21] Appl. No.: 824,979

[22] Filed: Jan. 31, 1986

[51] Int. Cl.[4] ..... A01H 5/00

[52] U.S. Cl. ..... Plt./86

[58] Field of Search ..... Plt./86

*Primary Examiner*—Robert E. Bagwill

*Attorney, Agent, or Firm*—Schwartz, Jeffery, Schwaab, Mack, Blumenthal & Evans

[57] ABSTRACT

A poinsettia plant named Mirabelle particularly characterized by the combined characteristics of creamy white colored bracts, dark green foliage, vigorous dwarf growth habit, early flowering, outstanding keeping quality, and by its commercially significant ability of being grown as a single stem or pinched plant.

1 Drawing Figure

The present invention relates to a new and distinctive cultivar of poinsettia plant known by the cultivar name Mirabelle, and botanically known as *Euphorbia pulcherrima.*

Mirabelle was developed by me through controlled breeding by crossing Mikkelsen Seedling No. 80-145-1 (seed parent)×Mikkelsen Seedling No. 79-702-3 (pollen parent). Mirabelle was given the breeding number 84-754-6.

Mirabelle has been asexually reproduced by me by cuttings in the greenhouses of Mikkelsens Inc., Ashtabula, Ohio, and has been found to retain its distinctive characteristics through successive propagations.

The following characteristics distinguish the new cultivar from its parents and from other poinsettias commercially known and used in the floriculture industry:

1. The bract color of Mirabelle is a creamy white while both Mikkelwhite (disclosed in U.S. Plant Pat. No. 2,731) and the unpatented cultivar White Rochford are a clearer white.

2. Mirabelle is a true genetic dwarf, with short internodes even under high humidity and temperature growing conditions, and is thus much more compact than all known existing white cultivars.

3. The leaf color is a darker green than both Mikkelwhite and White Rochford and is more lanceolate than the comparison cultivars. The leaf margin is almost entire with few undulations as compared to Mikkelwhite and White Rochford.

4. The flowers clusters (cyathia) remain very tight and do not grow apart as does both Mikkelwhite and White Rochford.

5. Rooting of cuttings occurs uniformly in 14 to 16 days at 21° C., which is similar to the comparison cultivars.

6. Mirabelle is similar to White Rochford and Mikkelwhite in breaking with new lateral shoots when the terminal meristem is removed; however, Mirabelle has stronger and thicker stems than the comparison cultivars and is not grassy.

7. Cyathia retention is average for a poinsettia cultivar and is similar to Mikkelwhite and White Rochford under stress of low light, high and low temperature, and low nutrients.

8. Bract number is slightly greater in the involucre than White Rochford and Mikkelwhite, but the involucre is smaller in diameter due to the genetic dwarf characteristics of this cultivar. Growing conditions can greatly influence the number and size of bracts.

9. The ease of flower initiation and development of cyathia and bracts even under stress environments is of economic importance to both the northern and southern grower. The dwarf characteristic will assist the southern grower in height control of the plant.

10. Under natural short days in Ohio, Mirabelle developed bracts and shed pollen three weeks earlier than White Rochford and Mikkelwhite. Under controlled day length using black-out cloth all cultivars flowered nearly the same, indicating that Mirabelle initiates flowers on a longer critical natural day length.

The accompanying colored photographic drawing, taken as a top view, illustrates the overall appearance of the new cultivar, with the colors being as true as possible to obtain in color reproduction of this type.

The following is a detailed description of the new cultivar based on plants produced under commercial practices in the greenhouses of Mikkelsens Inc., Ashtabula, Ohio, and photographed in December flowering. Color references are made to The Royal Horticultural Society Colour Chart except where general terms of ordinary dictionary significance are used.

Parentage: Controlled breeding by crossing Mikkelsen Seedling No. 80-145-1 (seed parent)×Mikkelsen Seedling No. 79-702-3 (pollen parent).

Propagation:

(A) *Type cutting.*—Stems, 60 to 70 mm.

(B) *Time to root.*—14 to 16 days, 12 to 14 hour day length at 21° C. summer; 16 to 18 days, 12 to 14 hour day length at 21° C. winter.

(C) *Rooting habit.*—Coarse, fibrous, numerous.

Plant description:

(A) *Form.*—Upright; when apical meristem is removed (pinching), leaving 5-6 nodes above the soil line of pot, generally 3 to 5 lateral shoots will emerge and develop into bracts.

(B) *Growth habit.*—Compact, genetic dwarf; stems are strong, holding bracts up for an excellent flowering display; growth is vigorous and early propagations may need to be controlled by growth regulators.

(C) *Foliage.*—Leaves are alternate and borne on 2.5 to 3.5 cm. long petioles that are light geeen in color. (1) Size: Mature leaves are 8 to 9 cm. long and 6 to 7 cm. wide at broadest point. (2) Shape:

Almost lanceolate with the leaf apices acute and the base truncate. (3) Texture: Glabrous, with veins sunken; under side rough with veins protruding. (4) Margin: Slightly undulate. (5) Color: Young foliage top side 137B; under side 137D. Mature foliage top side 137A and shiny; under side 137C.

Flowering description:

(A) *Flowering habits.*—Mirabelle flowers earlier than most commercial cultivars, apparently having a longer critical day length for flower initiation. Under controlled day length, development time is approximately 10 weeks. Mirabelle is the first white true genetic dwarf which is suited for growing as a pinched 10 cm. pot crop, or as blooming single stem plants in 6 cm. cells for use in planters. Mirabelle has good keeping qualities which allows the plant to be flowered early and held for later sale. The dark green leaves with white bracts offer an attractive contrast for a white flowered plant. Mirabelle can be produced without growth regulators or other means of restricting growth because of short internodes. There will have to be considerable research into the matter of flower initiation under natural day lengths coupled with temperatures, in comparison to controlled day length prior to initiation and at initiation. It is very apparent that Mirabelle is flowering earlier than most commercial cultivars under natural day length in Ohio but takes approximately the same time to develop when tested under exact controlled day lengths with other commercial cultivars. This characteristic of earlier flower initiation is of commercial significance.

(B) *Natural flowering season.*—The natural flowering season is mid to late November. Flowering time under controlled day length at 18° C. in summer is 10 weeks, and in winter is 10 weeks. The cyathia will continue to develop and initiate until day length is greater than 13 hours and temperatures are below 27° C.

(C) *Cyathia.*—Borne on 5 mm., light yellow-green stems; rounded in shape with one or possibly two nectar cups. Light green in color, becoming yellow at tips.

(D) *Borne.*—Involucre is almost flat with only slight reflexing. Cyathias stay tightly clustered at the center of the involucre without growing apart (splitting). Cyathia have a normal tolerance to stress of temperature, low light and low nutrition for remaining on the bract.

(E) *Quantity.*—Highly dependent on cultural practices and varies from 10 to more than 20. Cyathias continue to develop over several months.

(F) *Bracts.*—The last true leaves turn partially white, with most being green at the midrib and on the underside of the leaf. The primary bracts are 8 to 9 cm. long and 3.5 to 4.5 cm. wide with petioles 1 to 2 cm. long being oval in shape. Secondary bracts are 6 to 7 cm. long and 3 to 3.5 cm. wide on 0.5 to 1 cm. petioles as measured on a pinched plant. A non-pinched plant will have somewhat larger dimensions. The bract size will vary depending on nutrition, temperature, light and other cultural practices. On a pinched plant, the bract head diameter is 20 to 25 cm. and 15 to 20 bracts are produced. The number of bracts may vary up to 30 depending on age of plant and method of growing. Color: Young bracts, top side, 4D; under side 4D. Mature bracts, top side, between 11C and 11D; under side between 11C and 11C.

(G) *Reproductive organs.*—(1) Stamens: Numerous; anther oblong and yellow in color; filament white; pollen yellow. (2) Pistels: Stigma forked, color cream; styles cream; ovaries, 3 celled about 3 mm. when receptive and yellow-green in color. (3) Nectar cup: 1 or possibly 2 nectar cups are generally on each cyathia, yellow in color. Nectar is available on maturing cyathias.

Disease resistance: There is no evidence to date of mildew or botrytis problems. White fly has an apparent low preference to Mirabelle as adjacent infested cultivars did not cause buildup of egg masses on Mirabelle.

I claim:

1. A new and distinct cultivar of poinsettia plant named Mirabelle, as illustrated and described, and particularly characterized by its creamy white colored bracts; dark green foliage; vigorous, dwarf growth habit; early flowering; outstanding keeping quality, and by its commercially significant ability of being grown as a single stem or pinched plant.

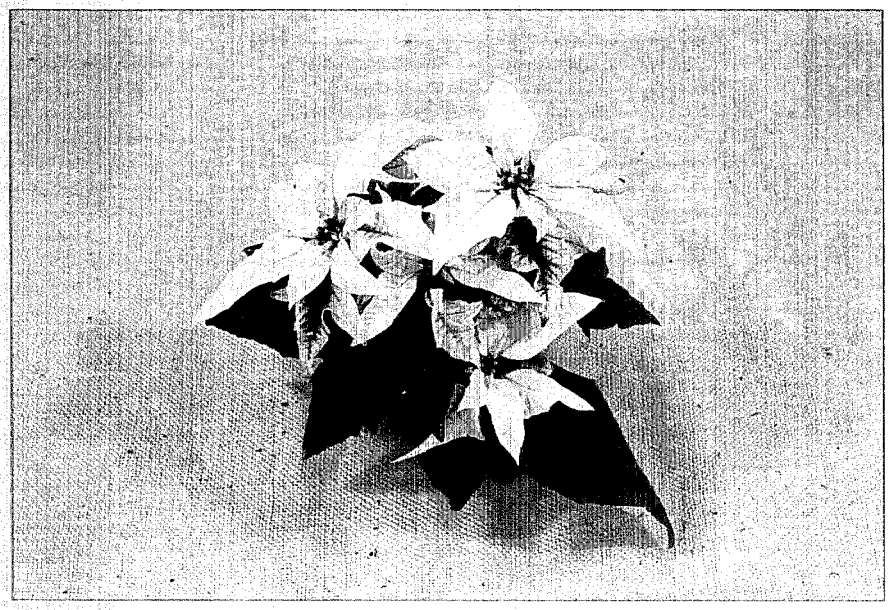

* * * * *